United States Patent
Merkine et al.

(10) Patent No.: US 10,453,257 B2
(45) Date of Patent: *Oct. 22, 2019

(54) SYSTEMS AND METHODS FOR NAVIGATING THROUGH AIRWAYS IN A VIRTUAL BRONCHOSCOPY VIEW

(71) Applicant: Covidien LP, Mansfield, MA (US)

(72) Inventors: Rahaf Merkine, Haifa (IL); Dorian Averbuch, Ramat Hasharon (IL); Elad D. Lachmanovich, Modin (IL)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/226,766

(22) Filed: Dec. 20, 2018

(65) Prior Publication Data

US 2019/0122434 A1    Apr. 25, 2019

Related U.S. Application Data

(63) Continuation of application No. 15/184,057, filed on Jun. 16, 2016, now Pat. No. 10,163,262.

(Continued)

(51) Int. Cl.
*G06T 15/00* (2011.01)
*G06T 19/00* (2011.01)
(Continued)

(52) U.S. Cl.
CPC .......... *G06T 19/003* (2013.01); *A61B 1/2676* (2013.01); *A61B 6/032* (2013.01);
(Continued)

(58) Field of Classification Search
CPC ......... G06T 19/00; G06T 17/20; G06T 17/00; G06T 15/10; G06T 15/00
(Continued)

(56) References Cited

U.S. PATENT DOCUMENTS 4,998,972 A    3/1991    Chin et al.
5,359,637 A    10/1994   Webber
(Continued)

FOREIGN PATENT DOCUMENTS

CN    1658789 A    8/2005
EP    0919956 A2   6/1999
(Continued)

OTHER PUBLICATIONS

MATLAB & Simulink, The B-form [online], Math Works, Feb. 19, 2014 [retrieved on Sep. 17, 2017]. Retrieved from the Internet: <URL:https://web.archive.org/web/20140219032522/https://www.mathworks.com/help- /curvefit/the-b-form.html>.

(Continued)

*Primary Examiner* — Gordon G Liu

(57) ABSTRACT

Systems and methods for displaying virtual bronchoscopy views while navigating through an airway of a virtual bronchoscopy are disclosed. The method comprises determining a first location and a first direction at the first location, storing the first location and the first direction in memory, displaying a first virtual camera view corresponding to the first location, determining a second location corresponding to movement through the airway of the virtual bronchoscopy, storing the second location in the memory, displaying a second virtual camera view corresponding to the second location, determining a second direction based on the first location and the second location, storing the second direction in the memory, determining a third location corresponding to further movement through the virtual bronchoscopy, and determining whether the further movement is in a forward direction or a backward direction.

19 Claims, 7 Drawing Sheets

Related U.S. Application Data

(60) Provisional application No. 62/181,824, filed on Jun. 19, 2015.

(51) Int. Cl.
*A61B 1/267* (2006.01)
*A61B 34/10* (2016.01)
*A61B 6/03* (2006.01)
*G06T 19/20* (2011.01)
*H04N 5/225* (2006.01)
*A61B 34/00* (2016.01)

(52) U.S. Cl.
CPC .............. *A61B 34/10* (2016.02); *G06T 15/00* (2013.01); *G06T 19/20* (2013.01); *H04N 5/225* (2013.01); *A61B 34/25* (2016.02); *A61B 2034/107* (2016.02); *G06T 2210/41* (2013.01); *H04N 2005/2255* (2013.01)

(58) Field of Classification Search
USPC ........................................................ 345/419
See application file for complete search history.

(56) References Cited

U.S. PATENT DOCUMENTS

| | | |
|---|---|---|
| 5,381,786 A | 1/1995 | Spears |
| 5,469,353 A | 11/1995 | Pinsky et al. |
| 5,513,101 A | 4/1996 | Pinsky et al. |
| 5,655,084 A | 8/1997 | Pinsky et al. |
| 5,699,798 A | 12/1997 | Hochman et al. |
| 5,734,384 A | 3/1998 | Yanof et al. |
| 5,782,762 A | 7/1998 | Vining |
| 5,854,850 A | 12/1998 | Linford et al. |
| 5,891,030 A | 4/1999 | Johnson et al. |
| 5,920,319 A | 7/1999 | Vining et al. |
| 6,081,577 A | 6/2000 | Webber |
| 6,083,162 A | 7/2000 | Vining |
| 6,201,988 B1 | 3/2001 | Bourland et al. |
| 6,212,420 B1 | 4/2001 | Wang et al. |
| 6,266,161 B1 | 7/2001 | Hara |
| 6,272,366 B1 | 8/2001 | Vining |
| 6,283,918 B1 | 9/2001 | Kanda et al. |
| 6,289,235 B1 | 9/2001 | Webber et al. |
| 6,349,373 B2 | 2/2002 | Sitka et al. |
| 6,366,800 B1 | 4/2002 | Vining et al. |
| 6,369,812 B1* | 4/2002 | Iyriboz ................. A61B 6/463 345/419 |
| 6,381,029 B1 | 4/2002 | Tipirneni |
| 6,381,557 B1 | 4/2002 | Babula et al. |
| 6,466,683 B1 | 10/2002 | Poor |
| 6,510,340 B1 | 1/2003 | Jordan |
| 7,640,050 B2 | 12/2009 | Glenn, Jr. et al. |
| 10,163,262 B2 | 12/2018 | Merkine et al. |
| 2003/0152897 A1 | 8/2003 | Geiger |
| 2005/0245803 A1 | 11/2005 | Glenn, Jr. et al. |
| 2006/0293558 A1 | 12/2006 | De Groen et al. |
| 2007/0052724 A1* | 3/2007 | Graham ................. G06T 19/003 345/620 |
| 2008/0074422 A1 | 3/2008 | Dekel et al. |
| 2008/0118117 A1 | 5/2008 | Gauldie et al. |
| 2008/0118135 A1 | 5/2008 | Averbuch et al. |
| 2011/0018871 A1 | 1/2011 | Shirahata |
| 2012/0136208 A1 | 5/2012 | Itai |
| 2012/0203067 A1 | 8/2012 | Higgins et al. |
| 2014/0281961 A1 | 9/2014 | Baker |
| 2015/0054929 A1 | 2/2015 | Ito et al. |

FOREIGN PATENT DOCUMENTS

| | | |
|---|---|---|
| JP | H10295639 A | 11/1998 |
| JP | H11313816 A | 11/1999 |
| JP | 2000051207 A | 2/2000 |
| JP | 2011139797 A | 7/2011 |
| JP | 2012110549 A | 6/2012 |
| JP | 2013517909 A | 5/2013 |
| JP | 2013192741 A | 9/2013 |
| JP | 2014124384 A | 7/2014 |
| JP | 2014180545 A | 9/2014 |
| JP | 2014230612 A | 12/2014 |
| WO | 2013171356 A1 | 11/2013 |

OTHER PUBLICATIONS

Extended European Search Report for EP 16 17 5122 dated Oct. 26, 2016.
Lin et al., "Slice-based virtual endoscopy navigation", IEEE Conf on Info Visualization, pp. 711-716 (2001).
Australian Examination report No. 1 for AU 2016/204103 dated Feb. 13, 2017.
Maeda Junichi et al., "Diagnosis by the virtual bronchoscope navigation", in Japanese Journal of Clinical Medicine (extra issue), saishin-haigangaku (latest study on lung cancer), Nippon Rinsyo, vol. 71, No. 6, pp. 383-387.
Office Action issued in corresponding Japanese application No. 2016-120830 dated Jun. 19, 2017.
Canadian Office Action dated Nov. 7, 2017 issued in corresponding Canadian application No. 2933503, 4 pages.
Notification of the First Office Action issued in Chinese application No. 201610445604.6 dated Jun. 4, 2018 with English translation, 12 pages.
Decision to Grant a Patent issued in Japanese Application No. 2017-212569 dated Aug. 10, 2018 with English translation, 6 pages.
Examination report No. 1 issued in corresponding Australian Application No. 2017232198 dated Aug. 28, 2018, 4 pages.
Japanese Office Action issued in corresponding Japanese applicaiton, JP 2018-168861, dated Jul. 12, 2019, together with English language translation (5 pages).

* cited by examiner

SYSTEMS AND METHODS FOR NAVIGATING THROUGH AIRWAYS IN A VIRTUAL BRONCHOSCOPY VIEW

CROSS REFERENCE TO RELATED APPLICATIONS

This application is a continuation application of U.S. patent application Ser. No. 15/184,057, filed on Jun. 16, 2016, which claims the benefit of and priority to U.S. Provisional Patent Application No. 62/181,824, filed on Jun. 19, 2015, the entire contents of each of which are incorporated herein by reference.

BACKGROUND

Technical Field

The present disclosure relates to systems and methods for displaying medical images in a dynamic and changing manner. More particularly, the present disclosure relates to systems and methods for dynamically displaying medical images during forward and backward movement in a virtual bronchoscopy during pathway planning based on a position and a direction of a virtual camera being navigated through airways of the lungs.

Discussion of Related Art

Pathway planning visualization techniques are rapidly growing in various medical areas. Visualization techniques help minimize the size of an incision, non-invasively treat diseases of a patient in surgeries, and non-invasively navigate inside of patients to identify and treat target lesions. However, visualization may pose unexpected risks when incorrect information is displayed. For example, when navigating a virtual camera view in a backward or retracting direction through an airway of the lungs, the views provided to a clinician may make it difficult for the clinician to retrace the previously taken steps and return to a previous location. Moreover, a user may find the virtual camera view navigating outside of the airways of the lungs.

SUMMARY

In one aspect, the present disclosure features a method for displaying virtual bronchoscopy views while navigating through an airway of a virtual bronchoscopy. The method includes determining a first location and a first direction at the first location, storing the first location and the first direction in memory, displaying a first virtual camera view corresponding to the first location, determining a second location corresponding to movement through the airway of the virtual bronchoscopy, storing the second location in the memory, displaying a second virtual camera view corresponding to the second location, determining a second direction based on the first location and the second location, storing the second direction in the memory, determining a third location corresponding to further movement through the virtual bronchoscopy, and determining whether the further movement is in a forward direction or a backward direction.

If it is determined that the further movement is in the forward direction, the method includes displaying a third virtual camera view corresponding to the third location. And If it is determined that movement is in the backward direction, the method includes retrieving the stored first direction and the stored second direction from the memory, determining a smoothing vector based on the stored first direction and the stored second direction, obtaining a smoothed virtual camera view based on the smoothing vector, and displaying the smoothed virtual camera view.

In embodiments, determining whether the further movement is in a forward direction or a backward direction includes determining a next pointer location and a current pointer location on a virtual bronchoscopy screen, calculating the difference between a coordinate of the next pointer location and a coordinate of the next pointer location. If the calculated difference is positive, determining that the further movement is in the backward direction. And if the calculated difference is negative, determining that the further movement is in the forward direction.

In embodiments, the first location, the second location, and the third location are determined based on the location of a pointer or cursor on a screen which is displaying the virtual camera views. In yet another embodiment, the method further includes that if it is determined that the further movement is in the forward direction determining a third direction based on the second location and the third location, and storing the third direction in the memory.

In embodiments, determining the smoothing vector includes determining a first vector based on the first location and first direction, determining a second vector based on the first location and the second direction, and averaging the first vector and the second vector to obtain the smoothing vector.

In embodiments, the spline is a spline of order two or a spline of order four. In embodiments, the method further includes receiving an input from a user which alters the first, second, third, or smoothed virtual camera views, and storing the altered first, second, third, or smoothed virtual camera view. In a further embodiment, determining the smoothing vector includes determining a vector having a direction between the first direction and the second direction.

In another aspect, the present disclosure features an apparatus for displaying virtual bronchoscopy views while navigating through an airway of a virtual bronchoscopy. The apparatus includes a network interface configured to receive position information of a navigation instrument from at least one position sensor of the navigation instrument, the position information including physical locations, a memory storing a plurality of virtual camera views of the virtual bronchoscopy, instructions, a first location, a first direction at the first location, a second location, and a second direction at the second location, a processor configured to execute the instructions. The instructions, when executed by the processor, cause the processor to determine whether movement through the airway of the virtual bronchoscopy is in a forward direction or a backward direction. If it is determined that the movement is in the forward direction, the instructions further cause the processor to determine a third location corresponding to the movement through the airway of the virtual bronchoscopy, and determine a third direction based on the second location and the third location. If it is determined that movement is in the backward direction, the instructions further cause the processor to retrieve the first direction and the second direction from the memory, and determine a smoothing vector based on the first direction and the second direction. The apparatus further includes a display configured to dynamically display, on a screen, images of a smoothed virtual camera view corresponding to the determined smoothing vector.

Any of the above aspects and embodiments of the present disclosure may be combined without departing from the scope of the present disclosure.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which.

DETAILED DESCRIPTION

Figure 1:
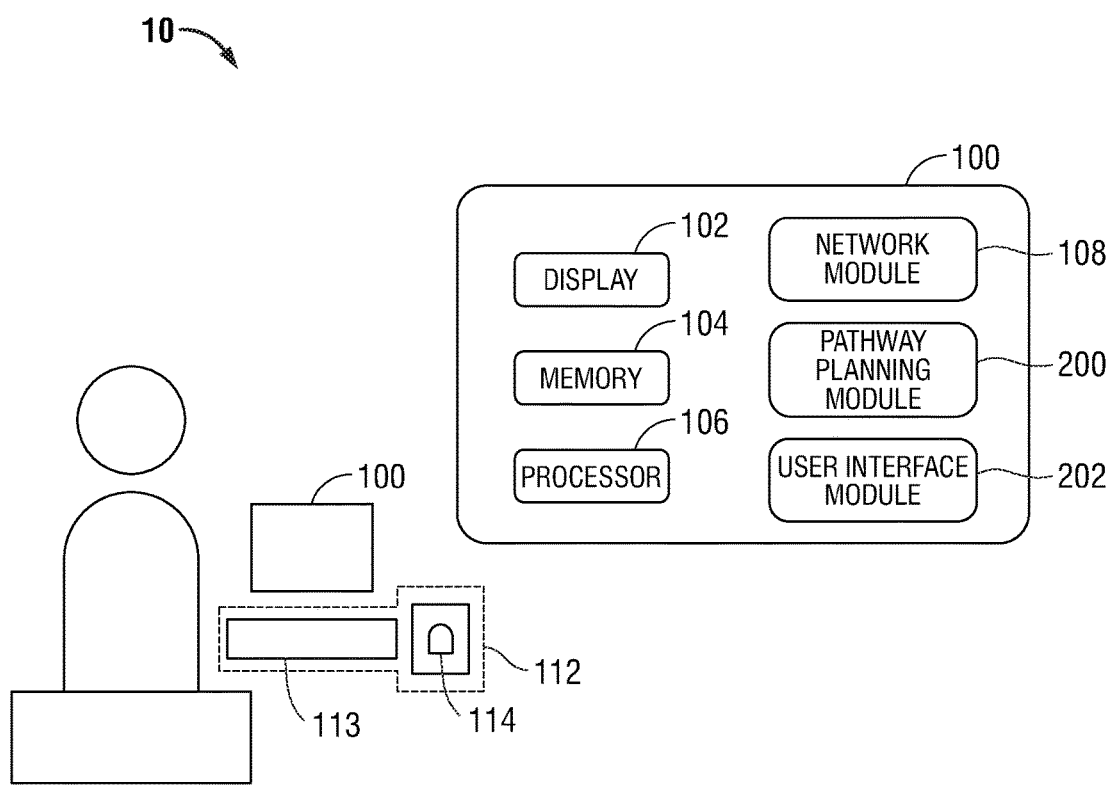
FIG. 1 is a schematic diagram of a computing device for pathway planning in accordance with an embodiment of the present disclosure.

The Virtual Bronchoscopy (VB) view enables a user to interact with a virtual camera (or point of view of the user) and to modify both the location and direction of the virtual camera view inside the airways of lungs. The movement backwards in the VB view could be achieved by adjusting the virtual camera (or user point of view) on one of the planar views (Axial, Coronal, Sagittal) and then going backwards in a straight line in the VB view. However, this method may involve at least two views and it may be difficult to retrace the actual steps and return to a previous location. Also, a user may find the virtual camera navigating outside the airways.

According to embodiments of the present disclosure, the movement forward, including turns, is recorded by storing each individual step in a stack and when the virtual camera moves backwards, its backward step is taken from the stack, therefore retaining both the actual location and direction of the virtual camera. Movement forward is performed by moving in straight lines. Movement sideways is performed by operating a data input device such as a mouse pointer at a position on the VB view and the center of the VB view updates to that position by way of animation to allow for a better user experience.

When the virtual camera view is turned (to the right or to the left) while moving forward in response to movement of a cursor or pointer on the screen and/or selection of a button by a user operating a user input device such as a mouse or touchpad, the turn takes place after a movement in a straight line is performed. The software saves a step or several steps forward in the stack and then a step with the turn. The step of the turn is performed in a single animation to provide a smooth turn. The animation is calculated based on the virtual camera's current location, current direction, the new rotation axis, and the delta in the 2D's x-axis of the view, i.e., changes in the left or right direction.

To provide a similar user experience when moving in a backward direction, the systems and methods according to the present disclosure record the location of the cursor or pointer on the display device after the cursor or pointer has been moved by a user via operation of a data input device such as a mouse, a touchpad, a trackball, or a touchscreen. As discussed herein, the x-coordinates and the y-coordinates of the location of the cursor or pointer on the display device is stored in a stack and used to determine forward and backward movement of the virtual camera. When the virtual camera moves backward, the current location and direction at the current location, along with the previous location and direction is taken from a stack. During or before backward movement, an average direction vector or other smoothing vector optimized for backward navigation is calculated for two adjacent steps (e.g., steps i and i−1) in the stack. In some embodiments, the smoothing vector is based on a spline or a Lanczos algorithm being applied to the first vector and the second vector. In the backward movement, the virtual camera view corresponding to the calculated average direction vector or other smoothing vector is used. This allows for smoother animation when performing turns while moving backward.

Referring now to FIG. 1, the present disclosure is generally directed to a pathway planning system 10 and method for planning a pathway through an anatomical luminal network of a patient for use during an operation. The pathway planning system 10 may include a computing device 100 such as, for example, a laptop, desktop, tablet, or other similar device, having a display 102, memory 104, one or more processors 106, and/or other components of the type typically found in a computing device. Display 102 may be touch sensitive and/or voice activated, enabling display 102 to serve as both an input and output device. Alternatively, a keyboard 113, mouse 114, or other data input device may be employed.

Memory 104 includes any non-transitory, computer-readable storage media for storing data and/or software that is executable by processor 106 and which controls the operation of the computing device 100. In an embodiment, the memory 104 may include one or more solid-state storage devices such as flash memory chips. In an alternative embodiment, the memory 104 may be mass storage device connected to the processor 106 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 106. That is, computer-readable storage media includes non-transitory, volatile and non-volatile, removable and non-removable media implemented in any method or technology for storage of information, such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computing device 100.

Computing device 100 may also include a network module 108 connected to a distributed network or the internet via a wired or wireless connection for the transmission and reception of data to and from other sources. For example, computing device 100 may receive computed tomographic (CT) images of a patient from a server, for example, a hospital server, an internet server, or other similar servers, for use during pathway planning. Patient CT images may also be provided to computing device 100 via a memory 104, which may be a removable memory.

A pathway planning module 200 includes a software program stored in memory 104 and executed by processor 106 of the computing device 100. As will be described in more detail below, pathway planning module 200 guides a clinician through a series of steps to develop a pathway plan for later use during a medical procedure. Pathway planning module 200 communicates with user interface module 202 for displaying visual interactive features to a clinician on the display 102 and for receiving clinician input.

As used herein, the term "clinician" refers to any medical professional (i.e., doctor, surgeon, nurse, or the like) or other user of the pathway planning system 10 involved in planning, performing, monitoring, and/or supervising a medical procedure involving the use of the embodiments of the systems, methods, and apparatuses described herein.

Figure 2:
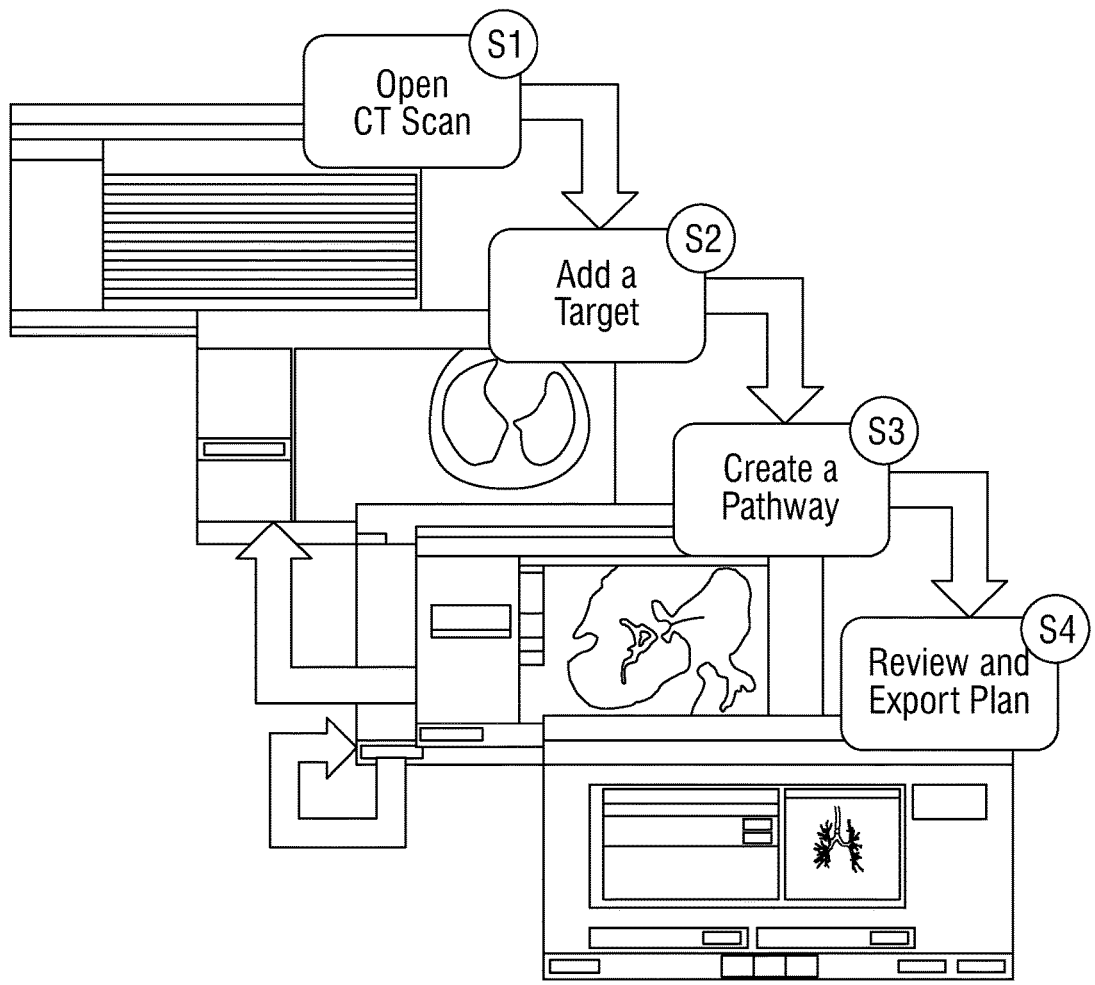
FIG. 2 is a diagram illustrating the four phases of pathway planning in accordance with the present disclosure.
Figure 6:
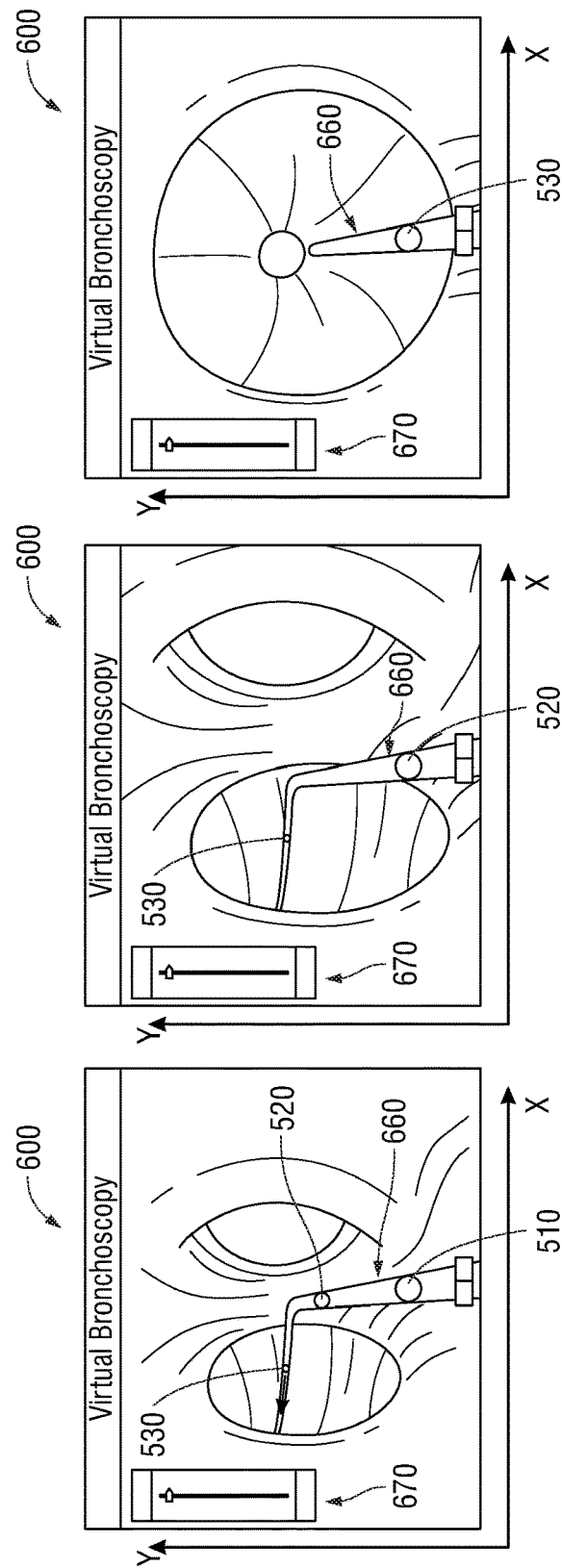

Referring now to FIG. 2, in an embodiment, pathway planning using the pathway planning module 200 may be performed in four separate phases. In a first phase S1, a clinician selects a patient for pathway planning. In a second phase S2, the clinician adds a target. In a third phase S3, the clinician creates the pathway to the target. Finally, in the fourth phase S4, the clinician reviews and accepts the plan and may export the plan for use in a medical procedure. The clinician may repeat either or both of the second and third phases S2 and S3 as needed to select additional targets and/or create additional pathways for a particular patient. For example, the clinician may select additional targets and may create a pathway to each target. The clinician may also or alternatively create multiple pathways to the same target. Once a pathway plan is generated, a virtual bronchoscopy view (illustrated in FIGS. 6A-6C) may be displayed, which allows a clinician to navigate within the virtual airways of the patient based on the pathway plan.

Figure 3:
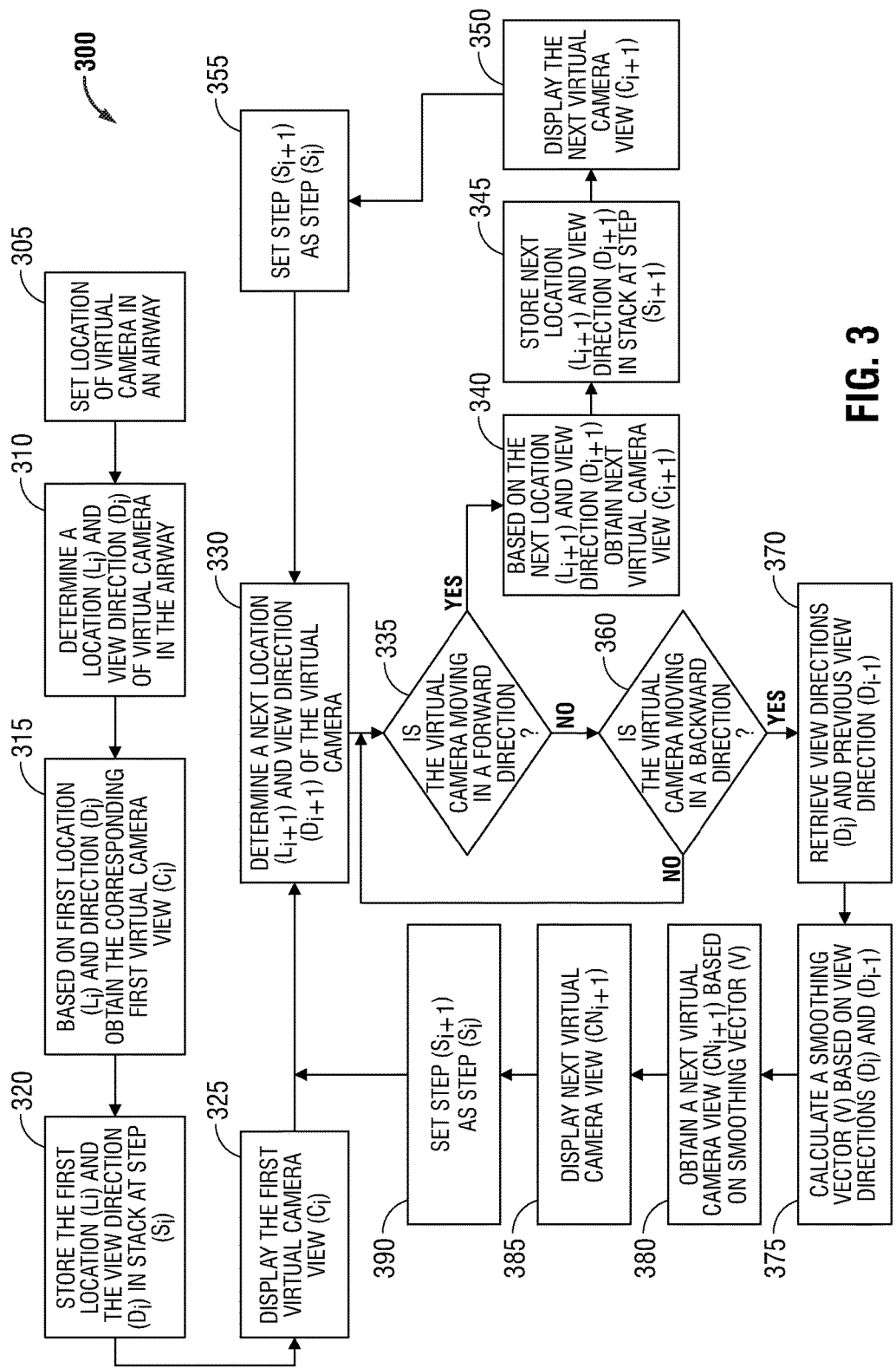
FIG. 3 is a flowchart illustrating a method for dynamically determining and displaying virtual camera views for forward and backward motion within lung airways according to an embodiment of the present disclosure.

FIG. 3 is a flowchart illustrating a method 300 for dynamically displaying virtual bronchoscopy views based on position and direction information of a virtual camera in accordance with embodiments of the present disclosure. At steps 305-310, a location pointed to by data input device 112 on display 102 within the virtual bronchoscopy view is displayed. In some embodiments, the location is set in a known airway such as the trachea or an entry point of the patient. The location pointed to by data input device 112 on display 102 is obtained as 2D x-coordinates and y-coordinates. The virtual location is utilized in order to generate a virtual camera view at the virtual location, at step 315. As the clinician progresses through the airways of the patient in the virtual bronchoscopy view, the clinician clicks or selects various locations within the airways to move forwards and backwards.

As the virtual location pointed to by data input device 112 (such as by using a pointer or cursor) on display 102 arrives at location $L_i$ at step 310 (as further described below with respect to FIG. 7) the view direction $D_i$ is utilized. Based on the location $L_i$, one or more processors 106 determine a view direction $D_i$ which corresponds to the location $L_i$. Location $L_i$ is a 2D coordinate having an x-coordinate and a y-coordinate, with respect to a position on display 102 of the airways.

Figure 7:
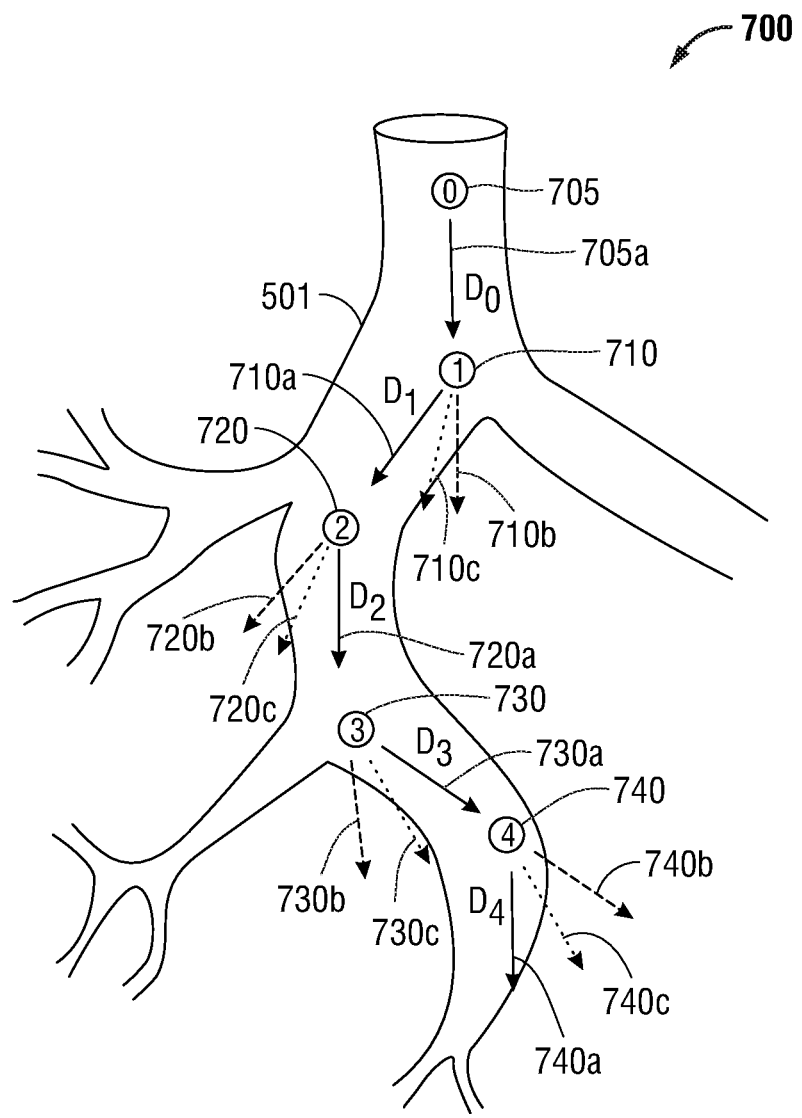
FIG. 7 is a graphical illustration of steps taken to navigate through lung airways in accordance with some embodiments of the present disclosure.

View direction $D_i$ may be expressed as a vector having a magnitude and an angle $\Theta_i$. Angle $\Theta_i$ may be defined as the difference between the angle of the current vector $\tilde{v}_i$ and the angle of the previous vector $\tilde{v}_{i-1}$ as illustrated in FIG. 7. For example, for a first vector $\tilde{v}_1$ extending from a first location $L_1$ to a second location $L_2$ and a second vector $\tilde{v}_2$ extending from the second location $L_2$ in a direction orthogonal to the first vector $\tilde{v}_1$, angle $\Theta_2$ of the second vector $\tilde{v}_2$ is 90°.

Once the location $L_i$ and view direction $D_i$ are determined, the one or more processors 106 obtain a virtual camera view $C_i$ from memory 104 based on the location $L_i$ and view direction $D_i$, at step 315. Virtual camera view $C_i$ is a 2D virtual image to be displayed in the virtual bronchoscopy window 600 (shown in FIGS. 6A, 6B, and 6C). Virtual camera view $C_i$ is a view inside the airways from the perspective of the tip of a virtual camera. Examples of the virtual camera view $C_i$ are shown in FIGS. 6A-6C.

At step 320, one or more processors 106 store the first location $L_i$ and view direction $D_i$ in memory 104, for example, within a stack or a lookup table at step $S_i$. An example of a lookup table (LUT) is shown below.

TABLE 1

| Step $S_i$ | Location $L_i$ | View Direction $D_i$ |
|---|---|---|
| i − 1 | $x_{i-1}, y_{i-1}$ | $\Theta_{i-1}$ |
| i | $x_i, y_i$ | $\Theta_i$ |
| i + 1 | $x_{i+1}, y_{i+1}$ | $\Theta_{i+1}$ |
| i + 2 | $x_{i+2}, y_{i+2}$ | $\Theta_{i+2}$ |
| i + 3 | $x_{i+3}, y_{i+3}$ | $\Theta_{i+3}$ |
| . | . | . |
| . | . | . |
| . | . | . |
| N | $x_n, y_n$ | $\Theta_n$ |

As used herein, the term location refers to the coordinate values and data which indicates the location of the pointer or cursor on display 102. View direction refers to the angle difference between the view in a straight line from the current location (a first vector) and the view in a straight line from the previous location (a second vector), as further illustrated in FIG. 7.

At step 325, virtual camera view $C_i$ is displayed on display 102 in the virtual bronchoscopy window 600, as shown in FIGS. 6A-6C. In some embodiments, a user may, by clicking a button on mouse 114 or depressing a key or a combination of keys on keyboard 113, alter and update the virtual camera view $C_i$. For example, the user may change the direction thereby displaying a new virtual camera view at a different view direction.

Forward Movement

Steps 330-355 of FIG. 3 illustrate movement of a virtual camera in a forward direction through the airways. At step 330, the next location $L_{i+1}$ and the next view direction $D_{i+1}$ of the virtual camera are obtained based on the location of the pointer or cursor on display 102. The next view direction $D_{i+1}$ may be determined by determining the direction of the vector extending from location $L_i$ to the next location $L_{i+1}$. At step 335, a determination is made as to whether the virtual camera has moved from location $L_i$ to next location $L_{i+1}$ in a forward direction, as described below with reference to FIG. 4.

If it is determined that the virtual camera is moving in a forward direction from location $L_i$ to next location $L_{i+1}$, the method proceeds to step 340. At step 340, once both the next location $L_{i+1}$ and view direction $D_{i+1}$ are determined, the one or more processors 106 obtains a next virtual camera view $C_{i+1}$ from memory 104 based on the next location $L_{i+1}$ and next view direction $D_{i+1}$.

At step 345, one or more processors 106 store the next location $L_{i+1}$ and next view direction $D_{i+1}$ in memory 104 at the next step $S_{i+1}$. At step 350, the next virtual camera view $C_{i+1}$ is displayed on display 102 in the virtual bronchoscopy window 600. At step 355, one or more processors 106 set the current location $L_{i+1}$ at next step $S_{i+1}$ to current step $S_i$, prior to returning to step 330 to determine next location $L_{i+1}$.

Backward Movement

In some embodiments, if, at step 335, it is determined that the virtual camera is not moving in a forward direction, the method proceeds to step 360. At step 360, it is determined whether the virtual camera is moving in a backward direction. Step 360 is used to confirm that the virtual camera is moving in a backward direction. Movement in a backward direction may be defined as movement to or near a previously-visited position. If, at step 360, it is determined that the movement is not in a backward direction, the method returns back to step 335 to determine whether movement of the virtual camera is in a forward direction.

If, at step 360, it is determined that movement is in a backward direction, the method proceeds to step 370. Based on the next location $L_{i+1}$, which is in a backward direction, the one or more processors 106 access a lookup table in memory 104 to determine the previous stored steps in the lookup table which corresponds to next location $L_{i+1}$. For example, if, at next location $L_{i+1}$, the coordinates are the processor would access the lookup table illustrated in Table 1 above and determine that previous locations $L_i$ and $L_{i-1}$ correspond to steps $S_i$ and $S_{i-1}$, respectively. Once steps $S_i$ and $S_{i-1}$ are determined, one or more processors 106, at step 370, obtain the view direction $D_i$ at step $S_i$ and the view direction $D_{i-1}$ at step $S_{i-1}$ from Table 1. Thus, for example, if it is determined that movement of the virtual camera is in a backward direction and the location corresponds to step $S_5$, one or more processors 106 obtain the view direction $D_4$ and the view direction $D_3$ from the lookup table illustrated in Table 1.

At step 375, one or more processors 106 calculate a smoothing vector V based on view direction $D_{i-1}$ and view direction $D_i$. As shown in Table 1 above, view directions $D_{i-1}$ and $D_i$ correspond to vector angles $\Theta_{i-1}$ and $\Theta_i$, respectively. In some embodiments, the smoothing vector is a new vector having an angle $\Theta N_{i+1}$, which bisects vector angles $\Theta_{i-1}$ and $\Theta_i$. Thus, for backward motion, by applying smoothing vector to angle $\Theta_i$ of view direction $D_i$, a new view direction at location $L_{i+1}$ is created with a new angle equal to $\Theta_i/2$.

In embodiments, the smoothing vector V is a vector that is based on (1) a first or previous vector defined by location $L_{i-1}$ and direction $D_{i-1}$, and (2) a second or current vector defined by location $L_i$ and direction $D_i$, and optimized for backward navigation so that, for example, the camera view does not leave the airway and/or the animation of the camera view appears smooth. The smoothing vector V may be a vector between the first and second vectors such as a vector that is the average or weighted average of the first and second vectors. The smoothing vector V may alternatively be determined by using a smoothing algorithm such as a spline or a Lanczos algorithm. The spline may be a quadratic spline (a spline of degree two) or a cubic spline (a spline of degree four).

After determining a new view direction $DN_{i+1}$ at location $L_{i+1}$ based on the smoothing vector, the one or more processors 106 determine, at step 380, a new virtual camera view $CN_{i+1}$ at location $L_{i+1}$. In some embodiments, location $L_{i+1}$ may be location $L_{i-1}$ or a location near location $L_{i-1}$. Thus, instead of using the original virtual camera view $C_{i+1}$ at location $L_{i+1}$, one or more processors 106 obtain the original virtual camera view $C_{i+1}$ from memory 104 and alter virtual camera view $C_{i+1}$ by the new view direction $D_{i+1}$ using the smoothing vector and generates new virtual camera view $CN_{i+1}$. At step 385, new virtual camera view $CN_{i+1}$ is displayed on display 102 in the virtual bronchoscopy window. Following step 385, one or more processors 106 set current location $L_{i+1}$ for step $S_{i+1}$ to step $S_i$, at step 390, prior to returning to step 330 to determine next location $L_{i+1}$.

Figure 4:
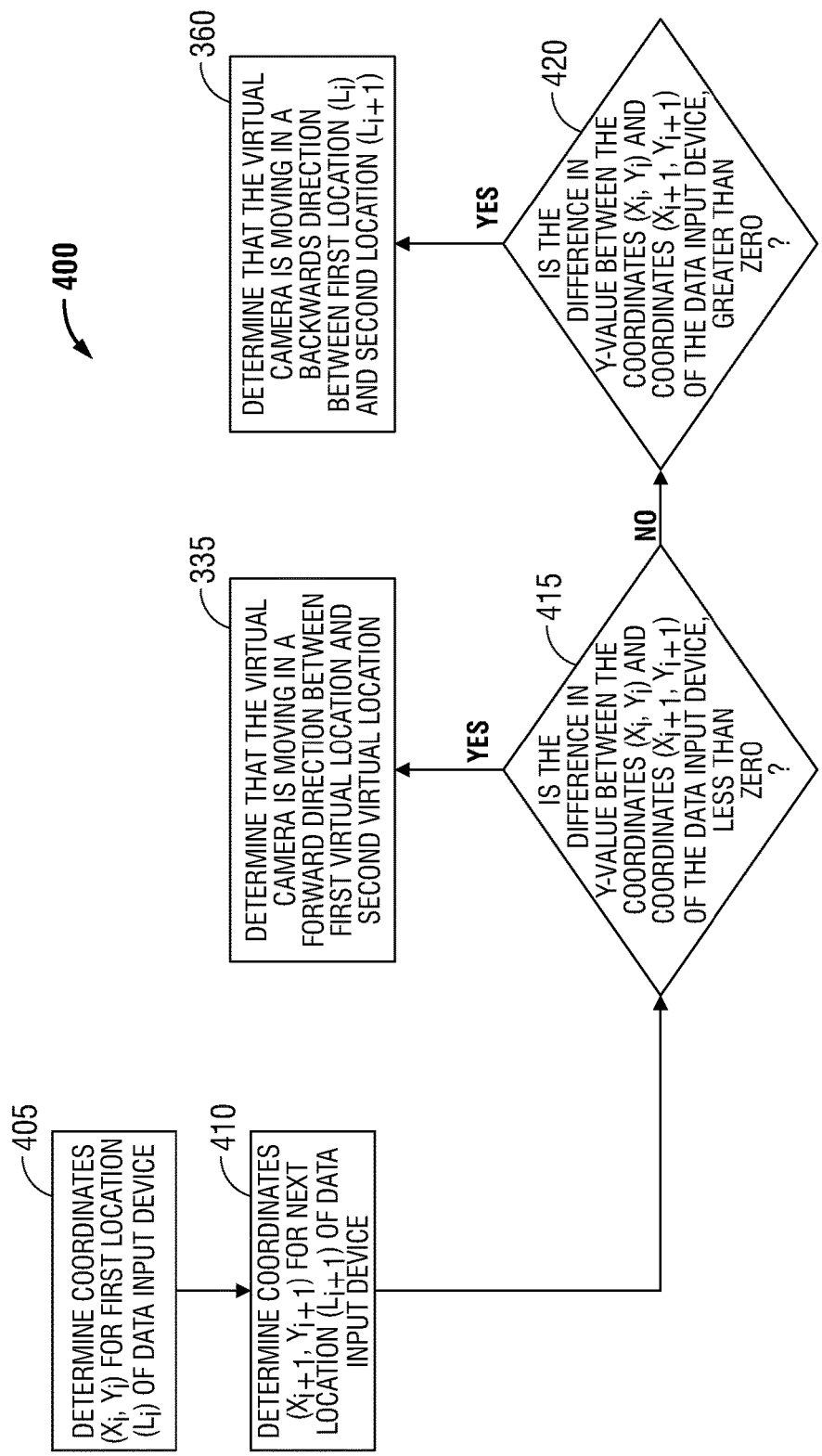
FIG. 4 is a flowchart illustrating a method of determining forward or backward direction within lung airways according to an embodiment of the present disclosure.

Turning now to FIG. 4, a flowchart illustrating a method 400 for the determination of forward and backward motion of steps 335 and 360 of FIG. 3 is described in greater detail. Using the current location $L_i$ and previous location $L_{i-1}$ of the pointer or cursor on display 102, a determination can be made of which directions, forwards or backwards, the virtual camera is moving at the current location $L_i$.

At step 405, one or more processors 106 obtain the 2D x-coordinates and y-coordinates of current location $L_i$ of the pointer on display 102. Next, at step 410, one or more processors 106 obtain the 2D x-coordinates and y-coordinates of next virtual location $L_{i+1}$ (which is moved from location $L_i$ by a user's operation of data input device 112) on display 102.

At step 415, one or more processors 106 determine whether the difference between the y-coordinate value of next location $L_{i+1}$ and the y-coordinate value of location $L_i$ of the pointer on display 102 is less than zero. If, at step 415, it is determined that the difference between the y-coordinate value of next location $L_{i+1}$ and the y-coordinate value of location $L_i$ is less than zero, then one or more processors 106 determine that the virtual camera is moving in a forward direction.

If, at step 415, it is determined that the difference between the y-coordinate value of location $L_{i+1}$ and the y-coordinate value of location $L_i$ of the pointer on display 102 is not less than zero, method 400 proceeds to step 420 where it is determined whether the difference between the y-coordinate value of next location $L_{i+1}$ and the y-coordinate value of location $L_i$ is greater than zero. If, at step 415, it is determined that the difference between the y-coordinate value of next location $L_{i+1}$ and the y-coordinate value of location $L_i$ is greater than zero, then one or more processors 106 determine that the virtual camera is moving in a backward direction.

Figure 5:
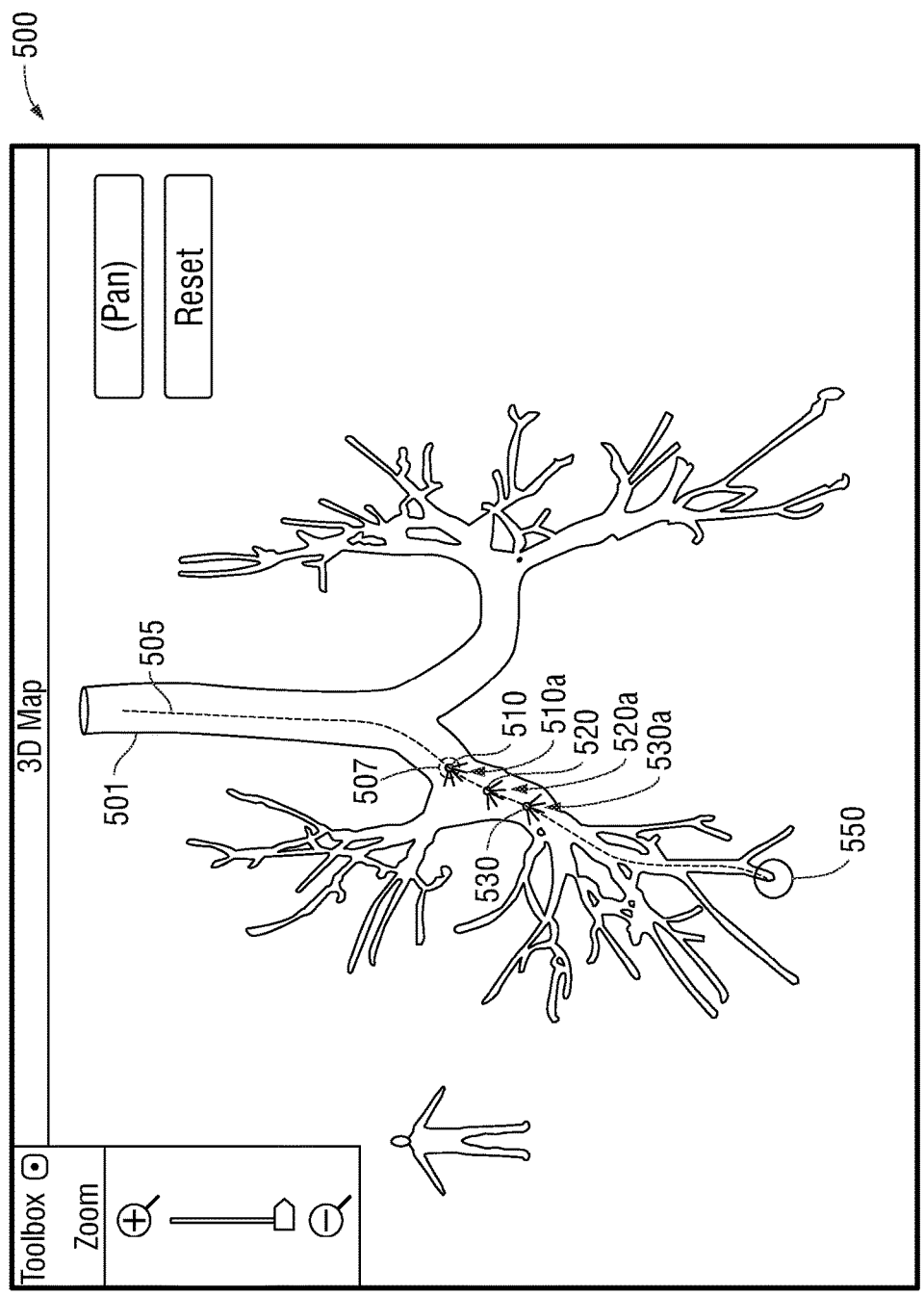
FIGS. 5 and 6A-6C are graphical illustrations of views while navigating within lung airways in accordance with an embodiment of the present disclosure.

Referring now to FIGS. 5 and 6A-6C, 3D map window 500 for a virtual bronchoscopy is displayed. When a target is identified and a pathway is identified by the computing device 100, a clinician may want to review the pathway in a navigation review mode. FIG. 5 illustrates the navigation review mode of the planning phase, in which computing device 100 shows a 3D map window 500 and a virtual bronchoscopy window 600 (FIG. 6A-6C) on the screen of display 102 in accordance with embodiments of the present disclosure.

The 3D map window 500 shows the 3D map and the virtual bronchoscopy window 600 shows virtual bronchoscopic video images. The 3D map window 500 displays and overlays a pathway 505 to a target 550 and a current position indicator 507. In the navigation review mode, the display 102 shows the virtual bronchoscopy window 600 as a fly-through view from the trachea to the target 550.

The virtual bronchoscopy window 600 also shows a pathway 660 toward the target 550 for review. The current position indicator 507 moves in the 3D map window 500 based on and in accordance with the current position shown in the virtual bronchoscopy window 600. In an aspect, the pathway 660 or 505 may not be displayed based on a display option that a clinician may set between showing the pathway and not showing the pathway.

The virtual bronchoscopy window 600 includes a slider 670 for opacity. By moving the slider 670, opacity of the virtual bronchoscopic video images may be changing from opaque to transparent. However, an opacity status of the virtual bronchoscopy is not synchronized with the 3D map shown in the 3D map window 500.

As shown in FIG. 5, airway passage 501 contains three camera views at three respective locations 510, 520, and 530. As the virtual camera navigates to target 550 at each of locations 510, 520, and 530, view directions 510*a*, 520*a*, and 530*a*, respectively, are displayed within virtual bronchoscopy window 600. Each view direction 510*a*, 520*a*, and 530*a* corresponds to the virtual bronchoscopic video images shown in FIGS. 6A, 6B, and 6C, respectively. As the virtual camera progresses from location 510 to 530, the view seen by a user is altered as shown in FIGS. 6A to 6C, respectively.

In FIG. 6A, a user is able to see, in virtual bronchoscopy window 600, pathway 660 containing locations 510, 520, and 530 along with the forking branches of airway passage 501. As the virtual camera approaches location 520 (FIG. 6B), the view shown in virtual bronchoscopy window 600 is approaching the forking branches. Once the virtual camera has reached location 530 (FIG. 6C), an airway passage is displayed at location 530. During forward motion, a user moves the pointer or cursor with an input device such as a mouse, keyboard, or touchpad, and selects locations forward along pathway 660, such as locations 510, 520, and 530. Thus, as a user notices forking branches, a user is able to select locations along pathway 660 which enter the forking branches, such as location 530. As each location is selected during forward motion, the virtual camera centers the view at that location. During backward motion, as the user moves the pointer or cursor and selects locations backward along pathway 660, the systems and methods of the present disclosure alter and smooth the view at the backward location, as opposed to displaying a virtual camera view centered at the backward location, thereby providing the user with a camera view which prevents the view the user sees in virtual bronchoscopy window 600 from being outside of the airway. For example, the systems and methods of the present disclosure will, for a user selecting backwards motion in the airway of FIG. 6C, prevent the view the user sees from being displayed as if the virtual camera was located outside of the airway at the forking branch of the airways.

FIG. 7 is a graphical illustration 700 of the airways and vectors associated with movement within the airways of the Virtual Bronchoscopy view. Graphical illustration 700 shows the vectors and smoothing vectors at various locations within the airways, such as locations 510, 520, and 530 of FIG. 6. As shown in FIG. 7, airway passage 501 contains five locations $L_0$-$L_4$ (705-740) and respective view directions $D_0$-$D_4$ (705*a*-740*a*). Each view direction 705*a*-740*a* is illustrated as a solid vector line extending from locations 705-740.

In the case of forward motion, as the virtual camera progresses from location $L_0$ to location $L_4$, the virtual camera view as seen by a user at each location 705-740 is displayed in a direction along view directions 705*a*-740*a*, respectively.

In the case of backward motion, for example, traversing locations 740-730-720, each view direction displayed at a previous location, e.g., 730*a* and 720*a*, is altered by smoothing vector. For example, for a smoothing vector that is the average of the current vector and a previous vector at the current location, altered view direction 730*c* is illustrated by a dotted line and is shown as a bisector of 730*a* and 730*b*. Altered view direction 730*c* is created as a bisector of the normal view direction 730*a* of location $L_3$ 730, and the view direction of previous location $L_2$ 720, which is illustrated by dashed line 730*b* extending from location $L_3$ 730.

Similarly, for backward motion from location $L_3$ 730 to location $L_2$ 720, altered view direction 720*c* is illustrated by a dotted line and is shown as a bisector of normal view direction 720*a* of location $L_2$ 720, and the view direction of previous location $L_1$ 710, which is shown as a dashed line 720*b* extending from location $L_2$ 720.

Although the present disclosure has been described in terms of specific illustrative embodiments, it will be readily apparent to those skilled in this art that various modifications, rearrangements and substitutions may be made without departing from the spirit of the present disclosure. For example, the determination of the smoothing vector is illustrated above as being performed online or dynamically during movement of the virtual camera. It is contemplated that in other embodiments smoothing vectors may be determined offline or prior to the start of the navigation mode at predetermined locations throughout the airways. This other embodiment may be beneficial when utilizing more complex methods for determining smoothing vectors or other vectors for optimizing the virtual camera view when moving in a backward direction. The scope of the present disclosure is defined by the claims appended hereto.

In addition to the aforementioned, reference is made to following commonly assigned applications, which describe features of image processing and user-interface updating, among other features which are relevant to the systems described herein: U.S. Provisional Patent Application No. 62/020,240, entitled "System And Method For Navigating Within The Lung," filed on Jul. 2, 2014; U.S. Provisional Patent Application No. 62/020,220 entitled "Real-Time Automatic Registration Feedback," filed on Jul. 2, 2014; U.S. Provisional Patent Application No. 62/020,177, entitled "Methods for Marking Biopsy Location," filed on Jul. 2, 2014; U.S. Provisional Patent Application No. 62/020,242, entitled "Unified Coordinate System For Multiple CT Scans Of Patient Lungs," filed on Jul. 2, 2014; U.S. Provisional Patent Application No. 62/020,245, entitled "Alignment CT," filed on Jul. 2, 2014, by Klein et al.; U.S. Provisional Patent Application No. 62/020,250, entitled "Algorithm for Fluoroscopic Pose Estimation," filed on Jul. 2, 2014; U.S. Provisional Patent Application No. 62/020,253, entitled "Trachea Marking," filed on Jul. 2, 2014; U.S. Provisional Patent Application No. 62/020,261, entitled "Lung And Pleura Segmentation," filed on Jul. 2, 2014; U.S. Provisional Patent Application No. 62/020,258, entitled "Cone View—A Method Of Providing Distance And Orientation Feedback While Navigating In 3D," filed on Jul. 2, 2014; U.S. Provisional Patent Application No. 62/020,262, entitled "Dynamic 3D Lung Map View for Tool Navigation Inside the Lung," filed on Jul. 2, 2014; U.S. Provisional Patent Application No. 62/020,261 entitled "System and Method for Segmentation of Lung," filed on Jul. 2, 2014; and U.S. Provisional Patent Application No. 62/020,257, entitled "Automatic Detection Of Human Lung Trachea," filed on Jul. 2, 2014. All these references are directed to aspects of processing the DICOM images, detecting the trachea, navigating within the lung, and displaying the DICOM images and processed images to provide enhanced clarity and performance for analysis, diagnosis, and treatment systems relating to, among other things, lung treatment planning and navigation. The contents of all the above-referenced applications are incorporated herein by reference.

What is claimed is:

1. A method for displaying virtual bronchoscopy views while navigating through an airway of a virtual bronchoscopy, the method comprising:
   determining a location corresponding to movement through the virtual bronchoscopy;
   determining whether the movement is in a forward direction or a backward direction;
   in response to determining that the movement is in the forward direction, displaying a forward virtual camera view at the determined location; and
   in response to determining that the movement is in the backward direction:
      retrieving a first direction and a second direction from memory;
      determining a smoothing vector at the determined location based on the first direction and the second direction;
      obtaining a smoothed virtual camera view based on the smoothing vector; and
      displaying the smoothed virtual camera view at the determined location.

2. The method according to claim 1, wherein determining whether the movement is in a forward direction or a backward direction includes:
   determining a next pointer location and a current pointer location on a virtual bronchoscopy screen;
   calculating a difference between a coordinate of the next pointer location and a coordinate of the current pointer location;
   in response to the calculated difference being positive, determining that the movement is in the backward direction; and
   in response to the calculated difference being negative, determining that the movement is in the forward direction.

3. The method according to claim 1, wherein the location is determined based on a location of a pointer or cursor on a screen which displays virtual camera views.

4. The method according to claim 1, wherein determining the smoothing vector includes:
   determining a first vector based on the first direction;
   determining a second vector based on the second direction; and
   averaging the first vector and the second vector to obtain the smoothing vector.

5. The method according to claim 1, wherein determining the smoothing vector includes:
   determining a first vector based on the first direction;
   determining a second vector based on the second direction; and
   applying a spline or a Lanczos algorithm to the first vector and the second vector to obtain the smoothing vector.

6. The method according to claim 5, wherein the spline is a spline of order two or a spline of order four.

7. The method according to claim 1, further comprising:
   receiving an input from a user which alters the forward virtual camera view or the smoothed virtual camera view; and
   storing the altered, forward virtual camera view or the altered, smoothed virtual camera view in the memory.

8. The method according to claim 1, wherein determining the smoothing vector includes determining a vector having a direction between the first direction and the second direction.

9. An apparatus for displaying virtual bronchoscopy views while navigating through an airway of a virtual bronchoscopy, comprising:
   a memory storing instructions, a plurality of virtual camera views of the virtual bronchoscopy, a first direction, and a second direction;
   a processor configured to execute the instructions,
   wherein the instructions, when executed by the processor, cause the processor to:
      determine whether movement through the airway of the virtual bronchoscopy is in a backward direction;
      in response to determining that the movement is in the backward direction:
         retrieve the first direction and the second direction from the memory; and
         determine a smoothing vector at a current location based on the first direction and the second direction; and
   a display configured to display, on a screen, an image of a smoothed virtual camera view corresponding to the determined smoothing vector at the current location.

10. The apparatus according to claim 9, wherein the current location is determined based on a location of a pointer on the screen.

11. The apparatus according to claim 9, wherein the instructions, when executed by the processor, further cause the processor to:
   determine a first pointer location and a second pointer location on the screen displaying a virtual camera view;
   calculate a difference between a coordinate of the first pointer location and a coordinate of the second pointer location; and
   in response to the calculated difference being positive, determine that the movement is in the backward direction.

12. The apparatus according to claim 9, wherein the instructions, when executed by the processor, further cause the processor to:
   determine a first vector based on the first direction;
   determine a second vector based on the second direction; and
   average the first vector and the second vector to obtain the smoothing vector.

13. The apparatus according to claim 9, wherein the instructions, when executed by the processor, cause the processor to determine the smoothing vector having a direction that is between the first direction and the second direction.

14. The apparatus according to claim 9, wherein the instructions, when executed by the processor, further cause the processor to:
   determine a first vector based on a first direction;
   determine a second vector based on a second direction; and
   apply a spline to the first vector and the second vector to obtain the smoothing vector.

15. The apparatus according to claim 14, wherein the spline is a spline of order two or a spline of order four.

16. A method for displaying virtual bronchoscopy views of an airway, the method comprising:
   determining a location corresponding to movement through the airway of a virtual bronchoscopy;
   determining whether the movement is in a forward direction or a backward direction;
   in response to determining that the movement is in the forward direction, displaying a forward virtual camera view at the determined location; and in response to determining that the movement is in the backward direction:
   obtaining a smoothing vector;
   obtaining a smoothed virtual camera view at the determined location based on the obtained smoothing vector; and
   displaying the smoothed virtual camera view at the determined location.

17. The method according to claim 16, further comprising:
   determining a first vector based on a first direction;
   determining a second vector based on a second direction; and
   averaging the first vector and the second vector to obtain the smoothing vector.

18. The method according to claim 16, further comprising:
   determining a first vector based on a first direction;
   determining a second vector based on a second direction; and
   applying a spline or a Lanczos algorithm to the first vector and the second vector to obtain the smoothing vector.

19. The method according to claim 18, wherein the spline is a spline of order two or a spline of order four.

* * * * *